United States Patent [19]

Hohorst et al.

[11] Patent Number: 4,997,822
[45] Date of Patent: Mar. 5, 1991

[54] HETEROCYCLIC COMPOUNDS HAVING A 2-(2-(N,N-BIS(2-CHLOROETHYL)-DIAMIDO-PHOSPHORYLOXY) ETHYL) RADICAL

[75] Inventors: Hans-Jurgen Hohorst, Marburg-Marbach; Ludmilla Bielicki, Frankfurt; Georg Voelcker, Nidderau-Windecken; Ulf Niemeyer, Bielefeld, all of Fed. Rep. of Germany

[73] Assignee: Asta Pharma Aktiengesellschaft, Frankfurt, Fed. Rep. of Germany

[21] Appl. No.: 16,915

[22] Filed: Feb. 20, 1987

[30] Foreign Application Priority Data

Feb. 22, 1986 [DE] Fed. Rep. of Germany ....... 3605847
Apr. 23, 1986 [DE] Fed. Rep. of Germany ....... 3613639

[51] Int. Cl.⁵ .................. A61K 33/42; C07F 9/22
[52] U.S. Cl. .................................... 514/90; 514/92; 544/53; 544/54; 544/55; 548/119
[58] Field of Search .................... 548/119; 514/90, 92; 544/53, 54, 55

[56] References Cited

U.S. PATENT DOCUMENTS

| | | | |
|---|---|---|---|
| 3,732,340 | 5/1973 | Arnould et al. | 260/936 |
| 3,794,730 | 2/1974 | Szabo | 514/90 |
| 4,368,196 | 1/1983 | Kiehs et al. | 514/90 |

*Primary Examiner*—John M. Ford
*Attorney, Agent, or Firm*—Cushman, Darby & Cushman

[57] ABSTRACT

There are disclosed compounds of the formula

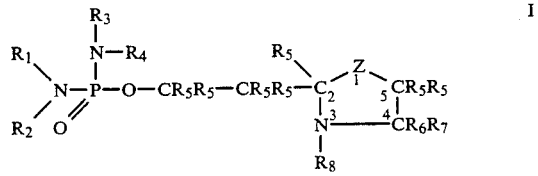

The compounds have antitumour and AIDS treatment activity.

6 Claims, No Drawings

HETEROCYCLIC COMPOUNDS HAVING A 2-(2-(N,N-BIS(2-CHLOROETHYL)-DIAMIDO-PHOSPHORYLOXY) ETHYL) RADICAL

SUMMARY OF THE INVENTION

The invention relates to compounds having the formula I

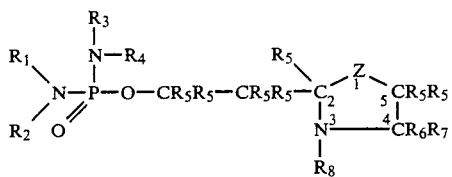

wherein the groups $R_1$, $R_2$, $R_3$ and $R_4$ are the same or different and represent hydrogen, $C_1$-$C_4$-alkyl, 2-chloroethyl, 2-bromoethyl or 2-$C_1$-$C_4$-alkanesulfonyloxyethyl and whereby at least two of these groups represent 2-chloroethyl, 2-bromoethyl or 2-$C_1$-$C_4$-alkanesulfonyloxyethyl, $R_8$ represents hydrogen, $C_1$-$C_6$-alkyl, $C_1$-$C_6$-alkoxycarbonyl, $C_2$-$C_6$ alkanoyl, the residue of a natural amino acid or of a natural dipeptide, free carboxyl groups present being optionally esterified by $C_1$-$C_6$-alkyl, or wherein $R_8$ represents aminocarbonyl or aminocarbonyl having one or two $C_1$-$C_6$-alkyl groups on the nitrogen atom. $R_6$ and $R_7$ represent hydrogen or taken together form an oxygen atom or wherein $R_6$ represents hydrogen, in which case $R_7$ represents a carboxyl group, a $C_1$-$C_6$-alkoxycarbonyl group, an aminocarbonyl group, a $C_1$-$C_6$-alkylaminocarbonyl group, a di-$C_1$-$C_6$-alkylaminocarbonyl group or a carboxylic acid amide group, whereby the amide moiety is a natural amino acid residue or a natural dipeptide residue or a $C_1$-$C_6$-alkylester thereof, Z represents a sulphur atom, an oxygen atom, the group $>NR_5$, the group $-S-C(R_5)_2-$, $-O-C C(R_5)_2-$ or $-NR_5C(R_5)_2-$ and the radicals $R_4$ are same or different and represent hydrogen or $C_1$-$C_6$-alkyl and salts thereof with physiologically acceptable acids or cations, processes for their production and medicaments containing compounds of formula I as active ingredients.

The compounds of the invention are highly active cytostatic agents having very low general and local toxicity (for example acute and subacute toxicity). In particular, the compounds of the invention also displays higher selectivity of cytotoxic activity on human tumour cells with lower bone marrow toxicity (i.e. in comparison to bone marrow toxicity). They therefore have, for example, a considerably greater therapeutic range as compared to the known cytostatic "cyclophosphamide" (3 -4 times greater). The compounds of the invention are, for example, also effective on a local or intracavity basis. In addition, the compounds of the invention are also suitable for the treatment of AIDS diseases.

The antitumour activity of the compounds of the invention is, for example, displayed in the following models bladder carcinoma in small nude mice (nu/nu mice); S180 ascites tumour/mice: Yoshida Ascites-tumour/rats; P815 mastocytoma of mouse, human tumour cells in the clonogenic assay in vitro.

In contradiction to activated "cyclophosphamide" and other cytostatically active oxazophoaphorins, liberation of the alkylating agent occurs at a surprisingly far slower rate in the compounds of the invention.

In addition, the compounds of the invention bring about a reinforcement of the immune defence system (they thus constitute biological response modifiers). This reinforcement of the immune defence system occurs at a very low dosage (for example 0.05 -5 mg per kg/body weight).

If at least two of the radicals $R_1$, $R_2$, $R_3$ and $R_4$ in formula I represents 2-chloroethyl, 2-bromoethyl or 2$C_1$-$C_4$-alkanesulfonyloxyethyl, it is in this case also possible for these radicals to be in each case the same or different, i.e. for example $R_3$ may be 2-chloroethyl and $R_1$ may be 2-methanesulfonyloxyethyl ($R_2$ and $R_4$=hydrogen).

If the radicals $R_1$, $R_2$, $R_3$, $R_4$, $R_5$ and $R_8$ represent $C_1$-$C_6$-alkyl, these are preferably methyl groups. Alkyl, alkoxy and alkanoyl groups occurring in formula I may be straight or branched. If $R_8$ represents a $C_2$-$C_6$-alkanoyl group, this is in preferably acetyl. Such an alkanoyl group may also contain an additional carboxyl group and/or amino group, whereby the carboxy group is advantageously located at the terminal C atom of the alkanoyl group ($\omega$-position) and an amino group presents located for example in the neighbouring position to the carboxyl group or in the neighbouring position to the CO group. Examples thereof are: $\alpha$ or $\gamma$ glutamyl radicals. If $R_7$ and/or $R_8$ represent $C_1$-$C_6$-alkoxycarbonyl the alkoxy group advantageously consists of one or two C atoms. If $R_7$ represents a $C_1$-$C_6$-alkylaminocarbonyl group, and if this contains an additional carboxyl group, the carboxyl group is preferably located in the 1-position of the alkyl radical. Alkyl radicals located at an aminocarbonyl group of formula I preferably have one or two C atoms.

Particularly favourable activity is displayed by compounds of formula I wherein Z is a sulphur atom or represents the group $-S-C(R_5)_2-$ (especially where $R_5$ represents hydrogen).

If $R_7$ represents a carboxylic acid amide group and the amide moity represents the radical of a natural amino acid or of a natural dipeptide, this natural amino acid or peptide is linked to the carboxylic acid group via an amino group or amino function of the amino acid (preferably via the $\alpha$-amino group). In this case $R_7$ may in particular represent the structure $-CO-NH-CH(R_{18})-CO-R_{19}$, wherein $R_{19}$ represents OH, $C_1$-$C_6$-alkoxy or the radical $NH-CH(R_{18})-COR_{20}$ and $R_{18}$ represents hydrogen, a $C_1$-$C_{10}$-alkyl group or a $C_1$-$C_{10}$-alkyl group which is substituted by a hydroxyl group, a $C_1$-$C_6$-alkoxy group, a mercapto group, a $C_1$-$C_6$-alkylthio group, a phenyl group, a hydroxyphenyl group, an amino-$C_1$-$C_6$-alkylthio group, an amino-$C_1$-$C_6$-alkyloxy group, an amino group, an aminocarbonyl group, a ureido group ($H_2NCONH$-), a guanidino group, a carboxy group or a $C_1$-$C_6$-alkoxycarbonyl group, or $R_{18}$ forms together with the structural moiety $-NH-CH-CO-R_{19}$ the 2-carboxy-pyrrolidinyl-1-radical (prolinyl-(1)-radical) or the 4-hydroxy-prolinyl-(1)-radical. $R_{20}$ represents OH or $C_1$-$C_6$-alkoxy.

If $R_8$ represents the radical of a natural amino acid or of a natural dipeptide, then this or the peptide is linked via the carboxy group with the nitrogen atom in the 3-position of the heterocyclic ring of formula I. $R_8$ then represents in particular the radical $-CO-CH(R_{21})-NHR_{22}$, wherein $R_{21}$ represents hydrogen, a $C_1$-$C_{10}$-alkyl group or a $C_1$-$C_{10}$-alkyl group which is substituted by a hydroxy group, a $C_1$–$C_6$-alkoxy group, a mercapto group, a $C_1$–$C_6$-alkylthio group, a phenyl group, a hydroxyphenyl group, an amino-$C_1$–$C_6$-alkylthio group, an amino-$C_1$–$C_6$-alkoxy group, an amino group, an aminocarbonyl group, a ureido group ($H_2NCONH$—), a guanidino group, a carboxy group or a $C_1$–$C_6$-alkoxycarbonyl group, or wherein $R_{21}$ represents the radical —CO—$(CH_2)_n$—CH(NHR$_{22}$)—CO—OR$_{23}$, wherein $R_{22}$ represents hydrogen, the group —CO—CH($R_{21}$)NH$_2$ or the group —CO—$(CH_2)_n$—CH(NH$_2$)—CO—OR$_{23}$ and $R_{23}$ represents hydrogen or $C_1$–$C_6$-alkyl and n represents the numbers 1, 2 or 3.

Particularly suitable radicals of such natural amino acids or dipeptides (racemate, D- and L- forms) are in particular those which are derived from the following amino acids: glycine, proline, phenylalanine, tyrosine.

If $R_7$ represents a carboxy group, the compounds according to the invention of formula I may also be present in the form of corresponding salts with physiologically acceptable inorganic or organic cations. Inorganic cations which may be used include for example: $NH_4^+$, cations of the alkali metals (Na, K), of the alkaline earth metals (Ca, Mg), of bismuth, aluminium or iron. Organic cations which may be used include for example, the cations of the following amines: primary, secondary or tertiary $C_1$–$C_6$-alkylamines, which may also contain a second amino group (such as, for example, ethylenediamine, N,N′-dibenzylethylenediamine), ethanolamines (ethanolamine, 2-dimethylaminoethanol, 2-diethylaminoethanol, choline, novocain), cyclic amines (for example $C_5$–$C_6$-cycloalkylamines such as cyclohexylamine), guanidine, piperidine, N-ethylpiperidine, piperazine, morpholine, N-ethyl-morpholine, nicotinamide, glucosamine, methylglucamine, theobromine, caffein, purine, imidazole. In addition, the cations of homocysteine thiolactone or α-amino-ε-caprolactam or a basic compound having the formula IV

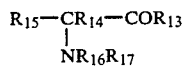

IV are also suitable. In formula IV, $R_{13}$ represents a hydroxy group, an amino group or a $C_1$–$C_6$-alkoxy group, $R_{14}$ represents hydrogen or a difluoromethyl group, $R_{15}$ represents hydrogen, an indolyl-(3)-methyl radical, imidazolyl-(4)-methyl radical, a $C_1$–$C_{10}$-alkyl group or a $C_1$–$C_{10}$-alkyl group which is substituted by a hydroxy group, a $C_1$–$C_6$-alkoxy group, a mercapto group, a $C_1$–$C_6$-alkylthio group, a phenyl group, a hydroxyphenyl group, an amino-$C_1$–$C_6$-alkylthio group, an amino-$C_1$–$C_6$-alkyloxy group, an amino group, an aminocarbonyl group, a ureido group ($H_2NCONH$—), a guanidino group, a carboxy group or a $C_1$–$C_6$-alkoxycarbonyl group, or $R_{15}$ form together with the structural moiety $CR_{14}(NR_{16}R_{17})$ the pyrrolidinyl-(2)-radical, the 4-hydroxypyrrolidinyl-(2)-radical or the 2-oxo-3-amino-3-difluoromethyl-piperidine group and the radicals $R_{16}$ and $R_{17}$ represent hydrogen or $C_1$–$C_6$-alkyl radicals.

Basic salt components which are particularly suitable are compounds of formula IV wherein $R_{13}$ represents the hydroxy group, the radicals $R_{14}$, $R_{16}$ and $R_{17}$ are hydrogen and $R_{15}$ represents hydrogen or a $C_1$–$C_4$-alkyl group, which can also be substituted by an amino group or a guanidino group (advantageously in the γ-or δ-position).

The alkyl groups, alkoxy groups or alkylthio groups present in formula IV may be straight or branched chain. The $C_1$–$C_{10}$-alkyl group advantageously contains 1–6 carbon atoms. In the case of the alkoxy groups and alkylthio groups these are advantageously those with 1–4, in particular 1–2 C atoms; the same applies in respect of the radicals $R_{16}$ and $R_{17}$, should these be alkyl radicals. Should $R_{15}$ in formula IV be an alkyl group which contains an amino-$C_1$–$C_6$-alkylthio-($C_1$–$C_6$-alkoxy) group, then these should advantageously be the following groups: $H_2N$—$CH_2$—$CH_2$—S—$CH_2$— or $H_2N$—$CH_2$—$CH_2$—O—$CH_2$—.

In the case of the compounds of formula IV these are advantageously compounds wherein $R_{13}$ represents a hydroxy group and the radicals $R_{14}$, $R_{16}$ and $R_{17}$ are hydrogen and $R_{15}$ can in particular have the meanings which are given therefore below.

Preferred basic compounds of formula IV are, for example, those where $R_{13}$ represents a hydroxy group, $R_{14}$ represents hydrogen or difluoromethyl, $R_{15}$ represents a $C_1$–$C_{10}$-alkyl group, in particular a $C_1$–$C_6$-alkyl group which (advantageously in the 2, 3, 4, 5 or 6 position; counting always commencing at the position where the alkyl radical is attached to the radical molecule) an amino group (in particular in the 3 or 4 position), an amino-$C_2$–$C_4$-alkylthio group, an amino-$C_2$–$C_4$-alkoxy group, a guanidino radical, an imidazolyl-(4)-methyl radical or an indolyl-(3)-methyl radical and $R_{16}$ and $R_{17}$ represent hydrogen or $C_1$–$C_4$-alkyl radicals; or aminoacid derivatives of the formula IV where $R_{13}$ represents an amino group or a $C_1$–$C_4$-alkoxy group, $R_{14}$ represents hydrogen, $R_{15}$ represents hydrogen, a phenylmethyl group, a 4-hydroxyphenylmethyl group or a $C_1$–$C_6$-alkyl group (preferably in the 2, 3, 4, 5 or 6 position) contains a hydroxy group, a mercapto group, a $C_1$–$C_4$-alkylthio group, an aminocarbonyl group, a $C_1$–$C_4$-alkoxycarbonyl group or ureido group and $R_{16}$ and $R_{17}$ represent hydrogen or $C_1$–$C_4$-alkyl residues.

In the case of the above mentioned amino acids or amino acid derivatives the salts are, for example, formed in each case from one mol of the compound I and one mol of the compound IV.

In addition, basic compounds of formula IV may, for example, be those wherein $R_{13}$ represents an amino group or a $C_1$–$C_4$-alkoxy group, $R_{14}$ represents hydrogen or difluoromethyl, $R_{15}$ represents a $C_1$–$C_{10}$-alkyl group, in particular a $C_1$–$C_6$-alkyl group which (preferably in the 2, 3, 4 or ω-position) contains an amino group, an amino-$C_2$–$C_4$-alkylthiogroup, an amino-$C_2$–$C_4$-alkoxy group, a guanidino radical, an imidazolyl-(4)-methyl radical or an indolyl-(3)-methyl radical and $R_{16}$ and $R_{17}$ represent hydrogen or $C_1$–$C_4$-alkyl radicals.

In the case of the last-named amino acid derivatives the salts are, for example, formed in each case from 2 mol of the compound I and 1 mol of the amino acid derivative of formula IV.

Individual examples of compounds of formula IV are: asparaginic acid diamide (DL-form), asparaginic acid diethylester (L-form), citrulline amide ($H_2N$—CO—NH—$(CH_2)_3$—CH(NH$_2$)—CONH$_2$, L-form), ornithine ethyl ester (L-form), arginine, arginine amide (L-form), 4-thialysine ($H_2N$—$CH_2$—$CH_2$—S—$CH_2$—CH(NH$_2$)—COOH), 2,6-diamino-enanthic acid (ε-methyl lysine), 4-oxalysine ($H_2N$—$CH_2CH_2$—O—$CH_2$—CH(NH$_2$)—COOH), glycinamide, N,N-dimethylglycinamide as well as the corresponding methyl or ethyl esters, prolineamide, hydroxyprolineamide, phenylalanineamide, the methyl or ethyl ester of alanine or of phenylalanine, homocysteinethiolactone (DL-form), α-amino-ε-caprolactam (D(+)-form), lysine (in particular L-lyaine), difluoromethyl-ornithine (DL- or L-form), valine methyl ester (L-form), threonine ethyl ester, histidine, histidine methyl ester, histidine amide, alanine amide, ornithine.

In the salts, in the event that in the compound IV $R_{13}$ represents an amino group or an alkoxy group and a basic group is also present or in the event that $R_{13}$ is an hydroxy group and two basic groups are also present, compound I (acidic components) compound IV (basic components) are present virtually in the proportion of 1:1. (This also applies should the basic component be homocyateine thiolactone or α-amino-ε-caprolactam). If, on the other hand, $R_{13}$ in the basic component IV is an amino group or an alkoxy group and should this also contain apart from the amino group in the α-position a further basic group, then in general the relationship between compound I and compound IV is 2:1. The salts of the invention are neutral salts. The pH of such salts ranges, for example, between 6–9, in particular 6–8.

Further salt components which come into consideration, for example, amines having the formula NR'R''R''', wherein the radicals R', R'' and R''' are the same or different and represent hydrogen or $C_1-C_4$-alkyl groups which may also contain a hydroxy group (for example oxyethyl). Individual examples of such amines are: methylamine, ethylamine, propylamine, isopropylamine, dimethylamine, diethylamine, triethylamine, trimethylamine, tripropylamine, methylethylamine, dimethylethylamine, diethylmethylamine, 2-hydroxyethylamine, bis-(2-hydroxyethyl)-amine, tris-(2-hydroxyethyl)-amine, (2-hydroxyethyl)-methylamine, (2-hydroxyethyl)-dimethylamine, bis-(2-hydroxyethyl)-methylamine, (2-hydroxyethyl)-ethylamine, (2-hydroxyethyl)-diethylamine, bis-(2-hydroxyethyl)-ethylamine, (2-hydroxyethyl)-methylethylamine. Cyclic amines which could, for example, be used are: morpholine, piperidine, pyrrolidine or piperazine and as diamines ethylenediamine or nicotinamide.

The compounds of the invention of formula I may also be present in the form of salts with physiologically acceptable acids. Acids of this kind may, for example, be: hydrohalic acids, e.g. hydrochloric acid, sulphuric acid, organic mono, di or tricarboxylic acids of the aliphatic, alicyclic, aromatic or heretocyclic series as well as sulphonic acids.

Examples of these are: formic, acetic, propionic, succinic, glycolic, lactic, malic, tartaric, citric, ascorbic, maleic, fumaric, hydroxymaleic or pyruvic acid; phenylacetic, benzoic, p-amino-benzoic, anthranilic, p-hydroxy-benzoic, salicylic or p-aminosalicylic acid, embonic acid, methanesulfonic, ethanesulfonic, hydroxyethanesulfonic, ethylene sulfonic acid; halogen benzene- sulfonic, e.g. p-chlorobenzene sulfonic, toluene sulfonic, naphthaline sulfonic acid or sulfanilic acid or also 8-chloro-theophylline.

Depending on the conditions of the process and on the starting materials one obtains the end products of formula I in free form (as basic compounds), as acids or in the form of their salts. The salts of the end products may be re-converted in using conventional processes for example with alkali, acids or ion exchangers into the bases or into compounds I respectively. From the latter it is possible to obtain salts by reaction with organic or inorganic acids or corresponding basic compounds, in particular those which are suitable for the formation of therapeutically acceptable salts.

Thus, for example, the carboxylic acids may be neutralized at 0°–20° C. in aqueous solution with a base, preferably sodium bicarbonate and the solution freeze-dried.

Amino acid salts, for example, lysine and arginine salts, may be obtained by addition of the equivalent amounts of the free amino acids to aqueous solutions of compounds of formula I having an initial pH of 4–5 at room temperature and subsequent lyophilization.

The exchange of the basic components of a salt of compound I against a basic component can, however, also be carried out using acidic ion exchangers which are loaded with a basic compound IV. Ion exchangers which may for example be used include polymers having matrix sulfonic acid groups or carboxylic acid groups. The matrix of the ion exchangers can, for example, be made up of a polystyrene resin, which may have a divinyl benzene content of from 2 to 16, preferably 4 to 8 (weight/weight) or of a phenol resin. The polystyrene ion exchanger is preferably in gel form. Loading of the ion exchanger with the basic components may, for example, be effected in the following manner: ½ml of ion exchange resin 1,2 mval/ml* in a column (ca. 4 cm diameter) having a cooling sleeve are regenerated with hydrochloric acid, washed until neutral and free of chloride ions with distilled water, treated with a 10% aqueous solution of the basic compound (220 mmol) IV and washed until neutral with distilled water.

* Manufacturers of ion exhangers quote the capacity of ion exchangers (i.e. the number of functional groups such as —$SO_3H$, —$CO_2H$) in mval/ml or mval/g of ion exchange resin.

THE PROCESS

The process is conducted in a solvent at temperatures between —70° and 100 ° C., preferably —10° to 80° C., in particularly 5° to 60° C., i.e. if desired with cooling, at room temperature or with heating. If X and Y of the starting compound II represent alkoxy groups or taken together form an alkylene dioxide group, reaction with the other starting component II is conveniently carried out in the presence of an acid catalyst, such as an inorganic or organic acid, such as for example trichloroacetic acid, p-toluene sulfonic acid, formic acid, hydrochloric acid, trifluoromethane sulfonic acid. If X and $R_4$ form the 6-ring (oxazophosphorinane ring) and Y represent hydroxy, alkoxy, alkylthio or the group —S—alk—$SO_3Z$, adjustment to the pH range favourable for the reaction, for example, pH 5–12, in particular 7–9, is by means of alkali hydroxides (NaOH). Solvents which may be used include for example: water, alcohols, in particular alkanols with 1–6 C atoms such as methanol, ethano., n-propanol, isopropanol or isobutanol, alkyl ketones with in each case 1–4 C atoms, such as in particular acetone, methylethyl ketone, aprotic solvents (such as dimethyl sulfoxide, acetonitrile, N-methyl-pyrrolidone, dimethyl formamide, hexamethylphosphoric acid triamide), halogenated hydrocarbons having 1–3 C atoms such as chloroform, ethylene dichloride, saturated cyclic ethers such as tetrahydrofuran, dioxan, saturated lower aliphatic ethers such as diethyl ether or similar solvents or mixtures of several of such solvents.

Introduction of the radcal $R_8$ by means of acylation according to the process for producing the compounds is effected by means of isocyanic acid, $C_1-C_6$-alkylisocyanic acid or by mean of an acid having the formula R—OH, whereby R is a $C_1-C_6$-alkoxycarbonyl group, an aminocarbonyl group, a $C_1-C_6$-alkylaminocarbonyl group, a di-$C_1-C_6$alkylaminocarbonyl group or a $C_2$–$C_6$-alkanoyl group or the radical of a natural amino acid or of a natural dipeptide and such an acid or dipeptide is preferably activated. Should such an activated acid be used for acylation purposes, these are preferably compounds of the formula R-W, wherein R has the meanings given above and W represents halgen (for example chlorine or bromine) but may also for example represent a group of the formula —OR′,—SR′ or a group of the formula —OSO$_3$H or —OCO—R″ and R′ represent a $C_1$–$C_6$-alkyl radical or also a phenyl radical, a phenyl radical substituted by nitro groups, $C_1$–$C_4$-alkoxy groups, $C_1$–$C_4$-alkyl groups or halogen atoms (chlorine, fluorine, bromine), a cyanomethyl radical or a carboxymethyl radical and R″ represents a straight or a branched chain $C_1$–$C_6$ *-alkyl group, a $C_1$–$C_6$-alkoxy group, a phenoxy group or a benzyloxy group, whereby R can also represent the group COCl, provided W represents halogen and in thia case a subsequent reaction in the conventional manner with NH$_3$*, a $C_1$–$C_6$-alkylamine or a di-$C_1$–$C_6$-alkylamine is carried out. If W represents a halogen atom, this is preferably chlorine, bromine or iodine; if R′ or R″ represents an alkyl group, halogenoalkyl group or alkoxy group, then thsse are preferably of low molecular weight and conveniently contain from 1 to 4 carbon atoms. Frequently, particularly when W represents a halogen atom or the group -OCOR″, the presence of an acid-binding substance such as alkali hydroxides, alkali carbonates, alkali bicarbonates, alkali acetates, alkaline earth carbonates, tertiary amines (trialkylamines such as triethylamine, pyridine) or also alkali hydrides and similar compounds is appropriate. Here the acid-binding agent may also be simultaneously used alone or in admixture with other convsntional materials as solvent (for example pyridine).

Should the free acid R-OH be used, it is necessary to activate it by means of the presence of condensation agents such as dicyclohexyl carbodiimide, tetraethyl pyrophosphite, 5-(3′-sulfonophenyl)-ethylisooxazole, sulfurous acid-bis-alkylamides (for example SO[N(CH$_3$)$_2$]$_2$), N,N′-carbonyldiimidazole etc. (Organic Reactions, Vol. 12, 1962, pages 205 and 239).

If R$_8$ represents a $C_1$–$C_6$-alkyl group, this may be introduced into such compounds of formula I wherein R$_8$ represents hydrogen by means of alkylation. Similarly. in compounds of formula I, wherein Z is the group NH or —NH—C(R$_5$)$_2$—, the hydrogen of this basic nitrogen atom may be replaced by means of alkylation by a $C_1$–$C_6$-alkyl group.

This alkylation may be effected for example by reaction with compounds of the formula $C_1$–$C_6$–alkyl-hal, ArSO$_2$O—$C_1$–$C_6$-alkyl and SO$_2$(O—$C_1$–$C_6$-alkyl)$_2$, whereby hal may be a halogen atom (in particular chlorine, bromine or iodine) and Ar an aromatic radical (for example a phenyl or naphthyl radical possibly substituted by one or several lower alkyl radicals). Examples are p-toluene sulfonic acid-$C_1$–$C_6$-alkyl ester, $C_1$–$C_6$-dialkyl sulphates, $C_1$–$C_6$-alkyl halides and the like. The alkylation reaction is conveniently advantageously conducted in the presence of conventional acid-binding agents. Acid-binding agents which may, for example, be used may the same as in the case of acylation.

Acylation or alkylation may for example be conducted at temperatures between −60° and 220° C., preferably −20° and 150° C., in particular +20° C. and 110° C. in inert solvents or suspension agents. Solvents or dispersing agents which may be used include, for example: aromatic hydrocarbons such as for example benzene, toluene, xylene; aliphatic ketones such as for example acetone, methylethyl ketone; halogenated hydrocarbons such as for example chloroform, carbon tetrachloride, chlorobenzene, methylene chloride; aliphatic ethers such as for example butyl ether; cyclic ethers such as for example tetrahydrofuran, dioxan; sulfoxides, such as for example dimethyl sulfoxide; tertiary acid amides, such as for example dimethylformamide, N-methylpyrrolidone, hexamethylphosphoric acid triamide; aliphatic alcohols much as methanol, ethanol, isopropanol, amyl alcohols, tertiary butanol, cycloaliphatic hydrocarbons, such as cyclohexane and the like. Aqueous mixtures of the solvents mentioned may also be used. The reaction is frequently carried out at the reflux temperature of the solvent or dispersing agent used. The alkylation reaction components are frequently used in excess. Alkylation may also be carried out in the presence of tetra-alkylammonium salts (in particular of halides) in combination with alkali hydroxides at temperatures between 0° and 100° C., preferably 20° to 80° in an aprotic solvent or also in chloroform or methylene chloride. Aprotic solvents which may be used include in particular tertiary amides (dimethyl formamide, N-methyl-pyrrolidone, hexamethyl phosphoric acid triamide), dimethylsulfoxide, acetonitrile, dimethyloxyethane, acetone, tetrahydrofuran. During acylation and alkylation one may also proceed by first producing an alkali compound from the compound to be reacted by reacting them in inert solvent such as dioxan, dimethyl formamide, benzene or toluene with an alkali metal, alkali hydrides or alkali amides (in particular sodium or sodium compounds) or butyl lithium at temperatures between 0° and 150° C. and for example then adding the acylating or alkylating agent (compound R-W, W=halogen).

In place of the listed alkylation and acylation agents it is possible also to use other equivalent agents conventionally used in chemistry (see for example also L. F. and Mary Fieser "Reagents for Organic Synthesis", John Wiley and Sons, Inc., New York, 1967, Vol. 1, pages 1303-4 and Vol. 2, page 471).

The acyl groups in the compounds of formula I can be split off again solvolytically whereby the corresponding compounds of formula I are obtained, wherein R$_8$ represents hydrogen. This solvolytic splitting off occurs for example by saponification with dilute acids or by means of basic substances (potashes, soda, aqueous alkali solutions, NH$_3$) at temperatures between 10° and 150° C., in particular 20° to 100° C.

The transfer of the radical R$_7$ into other possible meanings possible therefor may be effected by means of the following reactions:

(a) Saponification

Saponification consists in the conversion of compounds of formula I, wherein R$_7$ is a $C_1$–$C_6$-alkoxycarbonyl group, an aminocarbonyl group or an alkylamino or dialkylamino carbonyl group (in each case with alkyl radicals having 1-6 C atoms), into a compound of formula I wherein R$_1$ is the carboxyl group. This saponification is effected for example by means of water, dilute aqueous alkali alcoholic alkali or also possibly by means of mineral acids such as hydrochloric acid or sulphuric acid in alcoholic or aqueous-alcoholic solution at tempsratures between 20° and 200° C., preferably 20°-100° C. or also by means of NaCl/dimethylsulfoxide. Other inert solvents, such as dioxan, tetrahydrofuran, dimethylformamide, dimethylacetamide may also be used.

(b) Esterification

Esterification may for example be effected by reacting carboxylic acid salts of compounds of formula I ($R_7=CO_2H$), in particular alkali salts or silver salts, with $C_1-C_6$-alkali halides (chlorides, bromides, iodides) or by treating the free acids with $C_1-C_6$-diazoparaffines or $C_1-C_6$-aliphatic alcohols in the presence of acidic substances such as hydrochloric or sulphuric acid, chlorosulfonic acid, aromatic sulfonic acids (p-toluene sulfonic acid) or complex-forming materials such as boron trifluoride or zinc chloride or by the action of the corresponding acid halides of formula I $R_7=$COHal; Hal=Cl, Br, I) or acid anhydrides of formula I ($R_7=C_2-C_6$-alkanoyloxycarbonyl group) on $C_1-C_6$-alcohols, preferably in the presence of basic materials such as pyridine, triethylamine. alkali or alkaline earth metal hydroxides, -alcoholates, -carbonates or -acetates. This esterification is effected at temperatures between 20° to 250° C., in particular 60° to 100° C., with or without solvent. Solvents that may for example be considered are: aromatic hydrocarbons such as benzene, toluene, lower aliphatic alcohols, dimethylformamide, cyclic ethers, dimethylsulfoxide, N-methyl-pyrrolidone, sulfolan, chloroform, tetramethyl urea.

The above-mentioned halides ($R_7=$COHal) may for example be obtained by reaction with halogenating agents, such as phosphortri- and -penta- halides (chloride, bromide, iodide), thionyl halides (chloride, bromide, iodide), phosphorous oxyhalides (phosphorous oxychloride, phosphorous oxybromide), sulfuryl halides (sulfuryl chloride, sulfuryl bromide, sulfuryl iodide) or phosgen. The reaction may be conducted with or without solvents at temperatures between 20°–150° C., preferably 30°–100° C. Solvents that may be considered are inert agents such as dioxan, tetrahydrofuran, aromatic hydrocarbons (benzene, toluene), halogenated hydrocarbons (chloroform, methylene chloride). It is frequently appropriate to employ the corresponding starting acids ($R_7=CO_2H$) in the form of their alkali salts (sodium, potassium salts or also silver salts).

(c) The manufacture of the amides is effected by reaction with compounds of formula I, wherein $R_7$ is a carboxyl group or a $C_1-C_6$-alkoxycarbonyl group (possibly via the appropriate halide or anhydride) with ammonia, $C_1-C_6$-alkylamines, dialkylamines with alkyl groups having 1–6 C atoms, or the corresponding amino acids or dipeptides or correspondingly protected amino acids or protected dipeptides according to methods conventionally used in peptide chemistry. The reaction may for example be carried out in a conventional solvent or suspension material, whereby the solvents that may be considered are those already named. Water may also be used. Should compounds of formula I, wherein $R_7$ represents the —COHal group, be used as starting materials, acid binding materials (alkali metal hydroxides, alkali metal carbonates, alkali metal hydrogen carbonates, alkali metal acetates, alkaline earth metal carbonates, trialkyl amines, pyridine and similar) or also excess ammonia or amine may also be present. In so doing, the acid-binding agent may also be used alone or mixed with other conventional agents as solvent (for example pyridine). Should a compound of formula I be used as starting material, whereby $R_7$ is the carboxyl group, its activation is necessary in the presence of condensation agents such as dicyclohexyl carbodiimide, sulfurous acid-bis-alkylamides (for example SO[N(CH_3)_2]_2), N,N'-carbonyldiimidazole and the like (Organic Reactions Vol. 12, 1962, pages 205 and 239).

Should the manufacture of the amides be effected via the anhydrides, the latter may for example be obtained by reacting the salts (alkali salts, silver salts) of compounds of formula I, whereby $R_7$ is the carboxyl group, with the corresponding $C_2-C_6$-alkanoyl halides (chlorides, bromides, iodides) or by reaction of compounds of formula I, Wherein $R_7$ is —COCl, —COBr or —COI, with alkali metal salts or silver salts of the corresponding $C_2-C_6$-alkane carboxylic acids. These reactions are for example conducted in a solvent or suspension agent at temperatures between 20°–250° C.

Should the radical $R_7$ in the starting compound of formula III be a carboxy group, this may also be used in the form of a correspondingly common salt. If necessary the cation in the reaction product should then be exchanged for a physiologically acceptable cation. A starting compound II, wherein X together with $R_4$ represents a single bond and Y is a hydroxy group (for example 4-hydroxy-cyclophosphamide), may be manufactured in situ from the corresponding compound, wherein Y is hydrogen (for example cyclophosphamide) by means of conventional ozonization, for example in water, aqueous tetrahydrofuran or aqueous alcohol and then directly further reacted with a compound III. The ozonization conveniently conducted in the absence of hydrogen peroxide.

The isolation of products of the process is preferably effected by chromatographic processes, in particular by chromatography on silica gel or Sephadex (see Example 1c).

The products of the process may be stabilized by incorporation of thiols having a free SH group, such as cysteine, cysteamine, 2-mercapto ethanol. This is effected for example by dissolving the compounds of formula I in an aqueous solution of the thiol compound and then subjecting this mixture to freeze-drying. To effect such stabilization 0.02–0.05 mol of the thiol compound is for example used per 1 mol of compound I.

The starting materials of formula II, wherein X and Y each represent an alkoxy group or an alkylenedioxy ring are in part known for example from Japanese patent application No. 71/25140 (Japanese publication number 4738928) or may be obtained in a manner analagous to the method set out therein or as follows: reaction of phosphorous oxychloride with a corresponding acetal having the formula HO—C($R_5$)_2—C($R_5$)_2—C$R_5$XY (X,Y=$C_1-C_6$-alkoxy or O—(CH_2)_n—O with n =1–5) in an inert agent at low temperature (for example −20° to +10° C.) in the presence of a tertiary amine and subsequent reaction of the reaction product so obtained with the amines HNR_1R_2, HNR_3R_4 or ammonia in one or two steps, possibly in the presence of a tertiary amine at temperatures between −20° and 15° C. By analogy the starting materials of formula II, wherein X and Y each represent an alkylthio group or together represent an alkylene dithio ring may be manufactured bY reaction of phosphorous oxytrichloride with the corresponding thioacetal having the formula HO—C($R_5$)_2—C($R_5$)_2—C$R_5$XY (X,Y=$C_1-C_6$-alkylthio or —S—(CH_2)_n—S where n=1–5), and subsequently with the amines HNR_1R_2, HNR_3R_4 or ammonia in one step or two steps.

Starting materials of formula II, wherein X and Y together represent an oxygen atom may, for example be obtained from the corresponding hydroxy compounds (X=OH, Y=H) is known manner by oxidation (for example by analogy to D. Swern, J. Org. Chem. 43, 1978, page 2480; A. Myles et al, Tetrahedron Letters, 1977, page 2475; D. Swern, Synthesis, 1981, page 165; G. Piancatelli et al, Synthesis, 1982, page 245).

Furthermore such starting materials may be obtained from the corresponding thioacetals (X and Y=alkylthio or S—$(CH_2)_n$—S) in known manner by thioether splitting (for example by analogy to E. J. Corey, J. Org. Chem. 36, 3553 (1971) or from the corresponding oximes (X and Y==N—OH) or in known manner by oxime splitting (for example by analogy to J. H. Boyer, Chem. Rev. 80, 541 (1980), P. J. Mattingly et al, J. Org. Chem. 45, 410 (1980) and Synthesis 1976, 808).

Novel starting compounds of formula II may be manufactured according to conventional processes. For example, the esters of the carboxylic acids of formula II are obtained by reaction of the carboxylic acids with the corresponding alcohol in a hydrochloric acid medium. N-acetyl compounds are obtained by action of acetyl chloride or acetyl anhydride on the amino compound. For example to represent the N-acetyl cysteine the cysteine is converted with acetyl chloride into N,N'-diacetyl-cysteine and the reaction mixture reduced with zinc in acetic acid at 50°-60° C. N-alkyl compounds are for example obtained by reduction of the corresponding thiazolidine compounds. Thus, N-methyl cysteine is obtained by action of sodium on thiazolidine-4-carboxylic acid in liquid ammonia and hydrolysis of the reaction product with acid.

Products of the process of formula I are understood to be all possible stereoisomers and mixtures thereof. Taken individually, these are for example compounds which display different configurations at the phosphorus atom or at a C atom of the heterocyclic ring system.

Diastereomeric mixtures may be separated in known manner for example by means of fractional crystallization or by means of analytical and preparative high pressure liquid chromatography. The pure enantiomers may be obtained according to the customary methods of racemate splitting for example by fractional crystallization of diastereomeric salts.

It is possible for instance to consider optically active bases, such as 1-phenylethylamine, brucine, quinidine, strychnine and cinchonine for racemate splitting as well as other bases and methods which are described in "Optical Resolution Procedures for Chemical Compounds", Vol. 2, Paul Newman, 1981, Published by the Optical Resolution Information Center in Riverdale, USA. For this purpose one for example converts a racemate salt according to the invention in the already mentioned manner into a salt having a formerly mentioned optically active base, and separates the enantiomers in known manner.

The process can comprise, consist essentially of or consist of the stated steps with the recited materials. The compositions can comprise, consist essentially of or consist of the materials set forth.

DETAILED DESCRIPTION

EXAMPLE 1

2-{2-[N,N-bis(2-chloroethyl) -diamidophosphoryloxy]ethyl}-thiazolidine-4-carboxylic acid.

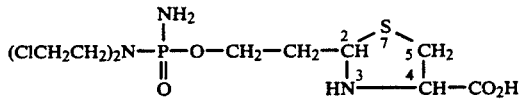

(a) Preparation from a compound of formula II, wherein X taken together with $R_4$ represents a single bond and Y represents a hydroxy group:

5.0 g (18 mmol) of 4-hydroxy-cyclophosphamide and 2.4 g (20 mmol) of L-cysteine in 12 ml of distilled water are mixed with 20 ml of 1N sodium hydroxide solution. The reaction mixture is stirred for 3 hours under a nitrogen atmosphere, concentrated below 0° C. in a high vacuum, the residue titrated with methanol/dichloromethane (3:2), the insoluble portion suction filtered off and the solution eluted several times on silica gel with methanol/dichloromethane (3:2).

The pure fraction having $R_f = 0.38$ (free carboxylic acid) was concentrated in vacuo, the residue treated twice with dry ether and finally dried to a glassy powder in a high vacuum.

Yield: 4.0 g (58% of theory).

The sodium salt may for example be obtained as follows: 1 g of the carboxylic acid 2-{2-[N,N-bis(2-chloroethyl)-diamidophosphoryloxy]ethyl}-thiazolidine-4-carboxylic acid, hereinafter sometimes referred to as D 18 038 is taken up in a little water, mixed with the equimolar amount of sodium bicarbonate and freeze-dried into a powder. Yield: 1.1 g (100% of theory).

Unless otherwise stated. the determination of the $R_f$ values is effected in a tank chamber with chamber saturation at room temperature: Stationary phase: aluminium foil coated with cellulose; the cellulose contains a fluorescence indicator.

Amount of substance applied: ca. 5 l of a solution of 10 mg/ml in methanol.

Eluting agent: water-acetonitrile 1:2.

Solvent run: 10 cm.

Identification is effected using the following special staining reagents: 4-(4-nitro-benzyl)-pyridine (reagent for alkylating groups) and ninhydrin spray test.

(b) Production from a compound of formula II, wherein X together with $R_4$ represents a single bond and Y is a $C_2$-alkoxy group (ethoxy group): To a solution of 4.6 g (15 mmol) of 4-ethoxy-cyclophosphamide in 10 ml ethanol is added a solution of 1.9 g (16.5 mmol) of L-cysteine in 24 ml of distilled water and 16 ml of 1 N sodium hydroxide solution. After 3 hours working up is effected as set out above.

Yield: 2.8 g (48% of theory).

$R_f = 0.38$ (free acid).

(c) Preparation from a compound of formula II, wherein both X and Y are each ethoxy:

1.05 g (3 mmol) 0-(3,3-diethoxy-propyl)-[N,N-bis-(2-chloroethyl)]-phosphoric acid diamide are suspended in a solution of 544 mg (4.5 mmol) of L-cysteine in ca. 20 ml 0.01 N HCl and warmed to 60° C. until a clear solution is formed (about 75 minutes). Following adjustment to a pH of 7 with NaOH the reaction solution is separated by gel filtration using a Sephadex G-10 column with 0.07M phosphate buffer as eluting solvent (Sephadex is a modified dextran medium for gel filtration in an aqueous polar medium). The fractions containing the reaction product are collected and also freed from salt by separation via a Sephadex G-10 column with $H_2O$ as eluting solvent. In so doing one obtains an aqueous solution of chromatographically pure reaction product D 18 038 which, when frozen at −20° C., may be kept for several days.

The concentration of the alkylans in the solution is determined using the NBP test [NBP= 4-(4-nitro-benzyl)-pyridine] and is on average 5 mg/ml, corresponding to a total amount of ca. 400 mg reaction product D 18 038 per batch (yield 35% of theory).

The following is another mode of operation with subsequent stabilization through addition of cysteine:

3 mmol (1050 mg) 0-(3,3-diethoxy-propyl)[N,N-bis-(2-chloroethyl)]-phosphoric acid diamide (aldophosphamide diethyl acetal) are dissolved together with 4.5 mmol (544 mg) of L-cysteine in 25 ml of 0.01 N formic acid. After 55 minutes at 57° C. shaking is effected three times with 25 ml chloroform. The chloroform residues are removed under a water jet vacuum (15 minutes). The aqueous solution is frozen and freeze-dried overnight. One obtains ca. 1 g of lyophilisate which is extracted with 60 ml peroxide-free tetrahydrofuran (cleaning via an aluminium oxide column immediately before use) at 4° C. (cold room) (shaking for 1 minute, then ultrasonic bath for 1 minute).

Following centrifugation (Sorvall RC5C centrifuge, 40,000 g, 15 minutes 4° C.) and concentration of the tetrahydrofuran supernatant fluid until dryness the residue is dissolved in a 0.32 mg/ml aqueous L-cysteine solution, whereby as much aqueous L-cysteine solution is used as is necessary to achieve a concentration of compound I of 20 mg per ml and this solution freeze-dried.

The preparations so produced contain 5 mol% 35 L-cysteine.

Yield ca. 200 mg substance D 18 038 (Yield ca. 18% based on the aldophosphamide diethyl acetal used).

The reaction product obtained according to methods (a)–(c) precipitates as a diastereomeric mixture. The O-(3,3-diethoxypropyl)-[N,N-bis-(2-chloroethyl)] phosphoric acid diamide which is used as a starting substance according to process example (c) may, for example, be obtained as follows:

3.6 g (23 mmol) phosphorous oxychloride in 25 ml dry methylene chloride are mixed dropwise at 0° to 5° C. over a period of 2 hours with stirring with a solution of 3.4 g (23 mmol) of 3-hydroxypropanaldiethylacetal in 10 ml methylene chloride and 3.3 ml triethylamine. Stirring is continued for one hour at 0° C. Subsequently 4.2 g bis-(2-chloroethyl)-aminehydrochloride are added and 7 ml triethylamine in 10 ml methylene chloride are added dropwise at 5°–10° C. The reaction mixture is stirred for one hour at 5° C. and left to stand at 4° C. The following day 2.8 g liquid ammonia in 5 ml methylene chloride are added dropwise with stirring. The temperature is allowed to rise to 20° C., stirring is continued for 3 hours, the product is washed with water, the organic phase dried over sodium sulphate and concentrated. The residue is chromatographed on silica gel with the aid of chloroform/methanol (10:1).

Yield: 3.9 g:

$R_f$-value: 0.6; (eluting solvent: benzene/chloroform/methanol =2:1:1, chamber saturation, length of run 15 cm, stain: iodine vapour, development at room temperature).

Production of the lysine salt:

For salt formation sufficient L-lysine is added which is equimolar to the concentration of the substance D 18 038 and the solution lyophilized in a freeze-dryer. The colourless lyophilisate so obtained is strongly hygroscopic, but can, unlike the free substance D 18 038, be stored for weeks unchanged with the exclusion of moisture at +4° C. The lysine salt still contains small amounts of the solvent (water) and is present as a diastereomeric mixture.

Thin layer chromatography of the lysine salt (during thin layer chromatography the salt is separated into L-lysine and the substance D 18 038, therefore with this method the $R_f$-values of these two components are obtained): cellulose-coated aluminium foil (thickness of layer: 0.1 mm);

Elution solvent water/acetonitrile 1:2

Substance D 18 038: $R_f$=0.68 L-lysine: $R_f$=0.08

Stability:

The lysine salt displays no changes in the chromatogram even after storage for weeks at −20° C.

Production of injectable solutions:

Solutions of 2-2-[N,N-bis-(2chloroethyl)-diamidophosphoryloxy] ethylthizolidine-4-carboxylic acid are produced immediately prior to use by incubating 4-hydroxy-cyclophosphamide for 45 minutes with a 10% excess of L-cysteine in 0.07 M phosphate buffer pH 7 at 37° C.

EXAMPLE 2

Ethyl 2-{2-[N,N-bis-(2-chloroethyl) diamidophosphoryloxy]ethyl}-thiazolidine-4-carboxylate (a) Preparation from a compound of formula II, wherein X together with $R_4$ represents a single bond and Y represents a hydroxy group: 5.0 g (18 mmol) of 4-hydroxycyclophoaphamide and 3.4 10 g (18 mmol) of ethyl L-cysteine-hydrochloride are stirred in 18 ml of water and 18 ml of 1 N sodium hydroxide solution in a nitrogen atmosphere for 4 hours. The reaction solution is shaken with dichloromethane and the organic phase washed with a little 0.1 N sulphuric acid and 3 times with water, dried over sodium sulphate and concentrated. The residue is treated with dry ether and concentrated in a high vacuum to a thin layer chromatographically uniform oil.

$R_f$ value=0.83 (conditions as for Example 1)

Yield: 4.8 g (65% of theory).

(b) Production from a compound wherein both X and Y are each an ethoxy group:

10 mg of O-(3,3-diethoxypropyl)-[N,N-bis(2-chloroethyl)]-phosphoric acid diamide and 8 mg of cysteine ethyl ester hydrochloride are heated in 1 ml 0.01N HCl to 56°.

After 60 minutes the acetal has completely disappeared and a new peak ($R_f$ value: 0.83) has formed in the thin layer chromatogram. The working up of the solution of the reaction is effected as set out under(a).

The product of the reaction obtained according to(a) or(b) consists in each case of a diamtereomeric mixture.

EXAMPLE 3

3N-acetyl-2-{2-[N,N-bis-(2-chloroethyl)-diamidophosphoryloxy]ethyl}-thiazolidine-4-carboxylic acid 10 mg of 0-(3,3-diethoxypropyl)-[N,N-bis(2-chloroethyl)]-phosphoric acid diamide and 7.5 mg of L-N-acetyl-cysteine are heated in 0.01N HCl at 56° C. The product is extracted with methylene chloride, the resulting methylene chloride phase dried over sodium sulphate, the methylene chloride removed, the residue taken up in methanol and chromatographed using a Sephadex LH 20 column with methanol as eluant (Sephadex LH 20 is a dextran three-dimensionally cross-linked with epichlorhydrin with hydroxypropyl groups which is used for gel filtration in organic solvents).

EXAMPLE 4

Methyl 2-{2-[N,N-bis-(2-chloroethyl)diamidophosphoryloxy]ethyl}-thiazolidine-4-carboxylate 1 g (~3 mmol) 0-(3-diethoxy-propyl) -[N,N-bis-(2-chloroethyl)]-phosphoric acid-diamide and 770 mg (4.5 mmol) L-cysteine methyl ester hydrochloride are heated in 20 ml 0.01N HCl for 75 minutes at 56° C. The reaction product is then neutralized with NaOH. The product is then extracted with 3×50 ml methylene chloride and the combined organic phase dried over sodium sulphate. Following concentration of the organic phase the yellow oil is taken up in water/methanol 1:1 and separated using a Sephadex G-10 column with 0.07 M phosphate buffer of pH 7.

The eluate, which contains the reaction product, is extracted with 3×250 ml methylene chloride and the methylene chloride phase concentrated. The residue is taken up in methanol and chromatographed over Sephadex LH20 with methanol as eluent. The fraction containing the reaction product is concentrated and dried in a high vacuum. A chromatographically pure yellowish-coloured oil is obtained which dissolves readily in polar organic solvents, less readily in apolar solvents and water. The reaction product is a diastereomeric mixture.

$R_f = 0.7$.

Yield: 200 mg (17% of the theoretical value).

EXAMPLE 5

2-{2-[N,N-bis-(2-chloroethyl)-diamidophosphoryloxy]ethyl}-4-oxo-thiazolidine 1 g (~3 mmol) of 0-(3,3-diethoxypropyl) [N,N-bis-(2-chloroethyl)]-phosphoric acid diamide and 730 mg (4.5 mmol) of N-(2-mercaptopropionyl)-glycine are heated in 20 ml of 0.01N HCl for 60 minutes at 56° C. The reaction product is then extracted with 3×50 ml of methylene chloride and the combined organic phase is dried over sodium sulfate. Following concentration of the organic phase the residue is taken up in methanol and chromatographed over a Sephadex LH20 column with methanol. A fraction is obtained which shows two newly formed, highly UV-aotive peaks. Following concentration of the eluate a yellow oil is obtained which is poorly soluble in water and apolar solvents. The reaction product is a diastereomeric mixture.

$R_f = 0.75$

Yield: 230 mg (19% of theory).

EXAMPLE 6

3N-L-γ-glutamyl-2-{2-[N,N-bis(2-chloroethyl)-diamidophos-phoryloxy]ethyl}-thiazolidine-4-carboxylic acid-(carboxymethylamide)

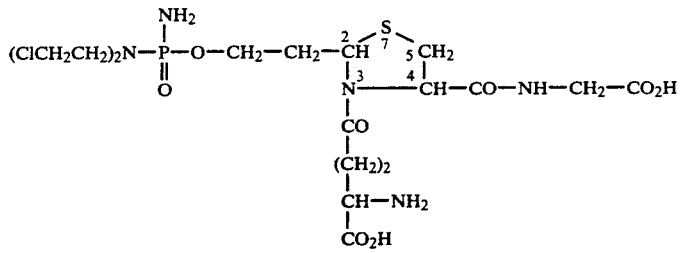

3 mmol (1.09 g) 0-(3,3-diethoxypropyl) [N,N-bis-(2-chloroethyl)]-phosphoric acid diamide are heated with 4.5 mmol (1.4 g) L-glutathion 25 ml of 0.01N formic acid for 60 minutes to 56° C. Subsequently the reaction mixture is extracted with 3×25 ml chloroform and lyophilized. Separation is via a silica gel column, wherein the silica gel presents octadecanyl groups ($C_{18}$-Reversed Phase Column), whereby the water is first separated out with glutathion. This is subsequently eluted with methanol and the glutathion-thiazolidone derivative is obtained.

Following removal of the methanol the reaction product is precipitated from water/ethanol 1:1.

Yield: ca. 200 mg; $R_f$ value: 0.48.

EXAMPLE 7

2-{1,1-dimethyl-1-[N,N-bis(2-chloroethyl)-diamidophorphoryloxy]ethyl}-thiazolidine-4-carboxylic acid

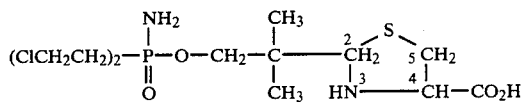

3 g of 0-[(3,3-diethoxy-2,2-dimethyl-propyl-(1)]-(N,N-bis-2-chloroethyl)-phosphoric acid diamide (8.5 mmol)] are suspended in a solution of 1.6 g of L-cysteine (13 mmol) in ca. 50 ml of 0.01N formic acid. Incubation is carried out for 30 minutes at 80° C. The product is extracted three times with 50 ml chloroform, the chloroform distilled off in vacuo and the product freeze-dried. A colourless solid material remains which consists essentially only of the thiazolidine reaction product and L-cysteine. In order to isolate the reaction product, the lyophilisate is extracted twice with 30 ml (in each case) of absolute tetrahydrofuran. The tetrahydrofuran extract yields 1.35 g relatively pure reaction product (>95%), corresponding to 38% of the theoretical yield. For final purification the substance may be applied to a reverse phase column (for example silica gel which is moistened with octadecanyl groups). The column may be flushed with $H_2O$ without the thiazolidine reaction product being eluted. The pure product may then be isolated using methanol-water (at least 20% methanol) or with pure methanol. The analytical data of the product of the process purified in this manner are:

| | Elementary analysis | | |
|---|---|---|---|
| | C | H | N |
| calculated | 35.29 | 5.88 | 10.29 |
| found | 34.99 | 5.74 | 10.01 |

High pressure liquid chromatography

Column $C_{18}$ Novo-Pak.

Eluting agent methanol/0.02N phosphate buffer pH 7 35:65.

One peak after ca. 15 minutes.
Thin-layer chromatogram
Cellulose on aluminium foil.
Eluting agent: acetonitrile/H2O 2:1.
R$_f$=0.89.

EXAMPLE 8

2-{2-[N,N-bis(2-chloroethyl)-diamidophosphoryloxy]ethyl}-homothiazolidine-4-carboxylic acid

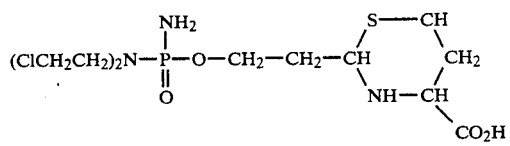

1.05 g (3 mmol) of 0-(3,3-diethoxypropyl) [N,N-bis(2-chloroethyl)]-phosphoric acid diamide and 4.5 mmol (0.61 g) DL-homocysteine are heated in 25 ml of 0.01N formic acid for 60 minutes at 56° C. The reaction mixture is then lyophilized and the lyophilisate taken up in 25 ml of tetrahydrofuran. The suspension is centrifuged and the residue concentrated in vacuo. The residue is taken up in tetrahydrofuran and mixed with an equimolar amount of concentrated hydrochloric acid. Following addition of ether reaction product (DL-form) is crystallized as the hydrochloride at −20° C. Melting point 136°–138° C. (decomposition).

R$_f$-value: 0.83 (stationary phase cellulose).

EXAMPLE 9

2-{2-[N,N'-bis-(2-chloroethyl)-diamidophosphoryloxy]-ethyl}-thiazolidine-4-carboxylic acid

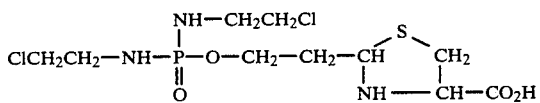

4.2 g (12 mmol) of N,N'-bis-(2-chloroethyl) phosphoric acid diamide-3,3-diethoxypropyl ester are incubated with 1.5 times the molar amount of L-cysteine in 100 ml 0.01N formic acid (1 hour at 60° C.).

The reaction mixture is extracted with chloroform and concentrated in a freeze-dryer.

The colourless powder which consists of about equal parts of the thiazolidine compound and L-cysteine is extracted with peroxide-free tetrahydrofuran (ca. 100 ml tetrahydrofuran/1 g thiazolidine compound). Following centrifuging off of the residue and concentration of the tetrahydrofuran solution the thiazolidine compound remains in the form of a colourless powder.

Thin-layer chromatography on cellulose plates.
Eluting agent: CH3CN/H2O 2:1.
R$_f$—0.86.

The starting material ethyl N,N'-bis-(2-chloroethyl)-phosphoric acid-3,3-diethoxypropionate may for example be obtained as follows:

chlorethylamine hydrochloride is suspended. At 0° C., 4 equivalents (one mol phosphoric acid-3,3-diethyoxy-propylester-dichloride) triethylamine are added dropwise to CH2Cl2 and left for 16 hours at ca. 5° C. with stirring. The precipitated hydrochloride is removed by shaking with ice water, the organic phase dried over sodium sulphate and extracted with active carbon. For further purification the product may be passed over a short silica gel column: eluting agent: methylene chloride.

EXAMPLE 10

2-{2-[N,N'-bis-(2--chloroethyl)-diamidophosphoryloxy]ethyl}1,5-perhydrothiazine(homothiazolidine)-4-carboxylic acid

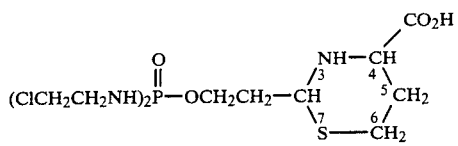

4.2 g (12 mmol) N,N'-bis-(2-chloroethyl)-phosphoric acid diamide-1,3-diethoxypropyl ester are incubated with a 1.5 times the molar amount of DL-homocysteine in 100 ml 0.01N formic acid (1 hour at 60° C. The reaction mixture is extracted with chloroform and concentrated by freeze-drying.

The colourless powder, which consists in about equal parts of the perhydrothiazinyl compound and DL-homocysteine, is extracted with peroxide-free tetrahydrofuran (ca. 100 ml tetrahydrofuran/1 g reaction product).

After centrifuging off the residue and concentration of the tetrahydrofuran solution the perhydrothiazinyl compound remains as a colourlesa powder.

Thin-layer chromatography on cellulose plate.
Eluting solvent: CH3CH/H20 2:1.
R$_f$=0.86.

The compounds of the invention display a good curative action in NMRI mice (female) with S-180 ascites tumour after a single intraperitoneal dose. For example, using the above mentioned experimental method, a dosage of 100 mg/kg mouse of the compound of Example 1 brought about a total cure in 5 out of 5 mice treated. The lowest dosage to effect a cure in the above mentioned animal experiment was in the region of 3 mg/kg given intraperitoneally.

A general dosage range of, for example, 10 mg/kg-200 mg/kg in particular 100 mg/kg given intraperitoneally, is possible to achieve a curative effect in the above mentioned animal experiment.

In the case of P 815 mastocytoma* ascites tumour in the BDF$_1$ mouse (male) the compounds of the invention display an increase in life span (ILS) of 136% and more when given intraperitoneally for example in a dosage of 1000 mg/kg body weight. The lowest effective dosage in this experiment is 100 mg/kg intraperitoneally. The general dosage range for a curative effect for P 815 ascites tumour is possibly for example: 100–1500 mg/kg given intraperitoneally or intravenously, in particular 1000 mg/kg. * tumour-like proliferation of atypical tissue mast cells.

The general activity of the compounds of the invention is comparable with the activity of the known medicament cyclophosphamide or ifosfamide. The following difference is, however, apparent: markedly diminished general toxicity, diminished bone marrow toxicity and absence of toxicity in the efferent urinary tract and in the bladder. In addition, the compounds of the invention, in contradistinction to cyclophosphamide or ifosfamide, are also effective in local or intracavitary application.

Example of the cytoatatic effect of 2-(2-[N,N-bis (2-chloroethyl)-diamidophosphoryloxy]ethyl)-homothiazolidine-4-carboxylic acid on P815 mastocytoma tumour in mouse:

Female BDF$_1$ mice were injected with $2 \times 10^6$ P815 mastocytoma cells intraperitoneally. The control animals (no cytostatic agent) died after 6.4 days (mean of 10 animals). On day 3 after tumour transplantation the treated animals received increasing doses of the compound of the invention:

| Dose mg/kg | ILS % after 28 days | Cure rate % after 40 days |
|---|---|---|
| 110 | 206 | 0 |
| 681 | 282 | 0 |
| 1000 | 352 | 30 |
| 1470 | 375 | 20 |

ILS = Increase of life span over untreated control. No of animals treated: 10/dosage.

Following an observation period of 40 days 30% (3/10) of the animals were definitively cured by the dosage 1000 mg/kg. In comparison thereto, all animals treated with an equally toxic dose receiving cyclophosphamine had died following an observation period of 28 days.

Following the fractionated administration of in each case 110 mg/kg of the compound according to the invention injected intraperitoneally daily for 6 days, 50% of the animals treated were, for example, still alive after an observation period of 6 weeks and thus definitively cured.

In addition to all forms of cancer, possible indications for the compounds of the invention also include the treatment of AIDS.

The acute toxicity of the compounds of the invention in the mouse (expressed in LD$_{50}$ mg/kg: method after Miller and Tainter: Proc. Soc. Exper. Biol. a. Med. 57 (1944) 261) lies for example in the region of 1000 and 3000 mg/kg in the case of intravenous application (generally above 1500 mg/kg).

The pharmaceutical formulations generally contain between 50 and 1500, preferably 150 to 500 mg of the active components of the invention.

Administration may, for example, be in the form of tablets, capsules, pills, coated tablets, suppositories, ointments, gels, creams, powder, dusting powder, aerosols or in liquid form. Possible liquid forms of application are, for example: oily, alcoholic or aqueous solutions as well as suspensions and emulsions. Preferred forms of application are tablets containing between 50 and 200 mg or solutions containing between 2 and 10% of active substance.

The individual dosage of the components of the invention can for example lie (a) between 0.5 to 7 g. preferably 1 to 3 g, in the case of oral medicinal forms, (b) between 100 mg to 5 g, preferably 0.5 to 2 g, in the case of parenteral medicinal forms (for example intravenous, intramuscular), (c) between 0.5 to 2 g, preferably 1 g, in the case of medicinal forms for inhalation (solutions or aerosols), (d) between 0.5 to 5 g, preferably 2 g, in the case of medicinal forms for rectal or vaginal application, (e) between 0.2 to 1.8 g, preferably 1 g, in the case of medicinal forms for local application on the skin and mucous membranes (for example in the form of solutions, lotions, emulsions. ointments etc.). (The doses are in each case related to the free base).

It is, for example, possible to recommend 1 to 10 tablets 3 times daily having a content of 150 to 700 mg active substance or, for example, in the case of intravenous injection 1 to 3 times daily one ampoule of 2 to 10 ml content with 50 to 2000 mg active ingredient. In the case of oral administration the minimum daily dose is for example 0.5 mg; the maximum daily dose for oral administration should not exceed 8 g.

For the treatment of dogs and cats, the oral individual dose generally lies between about 50 and 300 mg/kg body weight: the parenteral dose approximately between 15 and 200 mg/kg body weight.

For the treatment of horses and cattle, the oral single dose generally lies between about 50 and 200 mg/kg; the parenteral single dose about between 20 and 200 mg/kg body weight.

The acute toxicity of the compounds of the invention in mice (expressed in the LD 50 mg/kg: method after Miller and Tainter: Proc. Soc. Exper. Bio. a. Med. 57 (1944) 261) lies, for example. in the case of oral application between 1800 and 2400 mg/kg (or above 1800 mg/kg).

The medications may be used in human medicine, in veterinary medicine and in agriculture alone or in admixture with other pharmacologically active substances.

The compounds of the invention are furthermore also suitable for the treatment of AIDS diseases.

It has been shown that as a result of their structural analogy to the physiological substrate the compounds of the invention of formula I act as highly specific inhibiting agents for the enzyme responsible for the proliferation of lymphoid cells (in particular of T cells).

Thus the compounds of the invention of formula I may also be considered for the treatment of AIDS and its manifestations (for example Kaposi syndrome and the like): since the proliferation of the HTLV-III virus (AIDS virus) is bound to the presence and proliferation of specific lymphoid cells, in this case for example T$_4$ helper cells. compounds of formula I, through selective destruction of the T lymphocytes in the host organism possibly combined with an appropriate immune therapy and possibly in combination with bone marrow transplantation or adoptive immune therapy through transfer of interleukin-2 stimulating T cell subpopulations (the formation of which was stimulated by interleukin-2) are able to interrupt the proliferation cycle of the AIDS virus and thus cure the illness.

The compounds of formula I are able to act against the AIDS virus already in low dosage, for example in dosages of 0.05 to 5 mg/kg body weight.

Particularly in early stages of the disease and in conjunction with cytostatic treatment, compounds of formula I can, through specific inhibition of T suppressor lymphocytes, increase the ratio of T helper lymphocytes/T suppressor lymphocytes which is greatly diminished in AIDS and thus stimulate the immune defence system.

EXAMPLES FOR PHARMACEUTICAL FORMULATIONS

Lyophilisate of the compound according to Example 1

100 g of the compound according to Example 1 and 160 g of mannitol are dissolved in 4 liters of water for injection purposes under a nitrogen atmosphere and with the exclusion of light. The solution is filtered under sterile conditions through a suitable membrane filter and filled under aseptic conditions in 20 ml portions into 50 ml injection vials. The injection vials are fitted with freeze-drying stoppers and the contents freeze-dried. Subsequently the freeze-drying installation is ventilated with dry nitrogen and the injection vials closed inside the installation. The residual water content of the lyophilisate may not exceed 0.5%. In order to produce the solution for injection, the contents of the vial are dissolved in 20 ml water for injection purposes. The injection solution is isotonic. 1 ml of solution for injection contains 25 mg active substance.

Lyophilisate of the compound according to Example 1 With 5 Mol% cysteine 100 g of the compound of Example 1, 1.6 g of cysteine and 160 g of mannitol are dissolved whilst passing nitrogen and with the exclusion of light in 4 liters water for injection purposes. The solution is filtered under sterile conditions through a suitable membrane filter and filled under aseptic conditions into 50 ml injection vials in 20 ml portions. The injection vials are then fitted with freeze-drying stoppers and the contents freeze-dried. The freeze-drying inatallation is then ventilated with dry nitrogen and the injection vials closed inside the installation. The residual water content of the lyophilisate may not exceed 0.5%. In order to produce solution for injection, the contents of the vial are dissolved in 20 ml of water for injection purposes. The injection solution is isotonic. 1 ml of solution for injection contains 25 mg active substance and 0.4 mg cysteine.

The entire disclosures of German priority applications P3605847.5 and P3613639.5 are hereby incorporated by reference.

We claim:

1. A compound of formula:

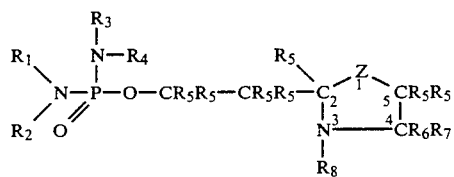

I wherein the groups $R_1$, $R_2$, $R_3$ and $R_4$ are the same or different and represent hydrogen, $C_1$–$C_4$-alkyl, 2-chloroethyl, 2-bromoethyl or 2-$C_1$–$C_4$-alkanesulfonyloxyethyl and whereby at least two of these groups represent 2-chloroethyl, 2-bromoethyl or 2-$C_1$–$C_4$-alkanesulfonyloxyethyl, $R_8$ represents hydrogen, $C_1$–$C_6$ alkyl, $C_1$–$C_6$-alkoxycarbonyl, $C_2$–$C_6$ alkanoyl, a radical of proline or a radical of —CO—CH($R_{21}$)— NHR$_{22}$, wherein $R_{21}$ represents hydrogen, a $C_1$–$C_{10}$-alkyl group or a $C_1$–$C_{10}$-alkyl group which is substituted by a hydroxy group, a $C_1$–$C_6$-alkoxy group, a mercapto group, a $C_1$–$C_6$-alkylthio group, a phenyl group, a hydroxyphenyl group, an amino-$C_1$–$C_6$-alkylthio group, an amino-$C_1$–$C_6$-alkoxy group, an amino group, an aminocarbonyl group, a ureido group ($H_2NCONH$—), a guanidino group, a carboxy group or a $C_1$–$C_6$-alkoxycarbonyl group, or wherein $R_{21}$ represents the radical —CO—($CH_2$)$_n$—CH(NHR$_{22}$)—CO—OR$_{23}$ and $R_{22}$ represents hydrogen, the group —CO—CH($R_{21}$)NH$_2$ or the group —CO—($CH_2$)$_n$—CH(NH$_2$)—CO—OR$_{23}$ and $R_{23}$ represents hydrogen or $C_1$–$C_6$-alkyl and n represents the numbers 1, 2 or 3, or $R_8$ represents a dipeptide of said radical of proline or said radical of —CO—CH($R_{21}$)—NHR$_{22}$, free carboxyl groups present being optionally esterified by $C_1$–$C_6$-alkyl, or wherein $R_8$ represents aminocarbonyl or aminocarbonyl having one or two $C_1$–$C_6$-alkyl groups on the nitrogen atom, $R_6$ and $R_7$ represent hydrogen or taken together form a ketone or wherein $R_6$ represents hydrogen, in which case $R_7$ represents a carboxyl group, a $C_1$–$C_6$-alkoxycarbonyl group, an aminocarbonyl group, a $C_1$–$C_6$-alkylaminocarbonyl group, a di-$C_1$–$C_6$-alkylaminocarbonyl group or a carboxylic acid amide group, whereby the amide moiety is a radical of —CO—NH—CH($R_{18}$)—CO—$R_{19}$, wherein $R_{19}$ represents OH, $C_1$–$C_6$-alkoxy or the radical NH—CH($R_{18}$)—COR$_{20}$ and $R_{18}$ represents hydrogen, a $C_1$–$C_{10}$-alkyl group or a $C_1$–$C_{10}$-alkyl group which is substituted by a hydroxyl group, a $C_1$–$C_6$-alkoxy group, a mercapto group, a $C_1$–$C_6$-alkylthio group, a phenyl group, a hydroxyphenyl group, an amino-$C_1$–$C_6$-alkylthio group, an amino-$C_1$–$C_6$-alkyloxy group, an amino group, an aminocarbonyl group, a ureido group ($H_2NCONH$—), a guanidino group, a carboxy group or a $C_1$–$C_6$-alkoxycarbonyl group, or $R_{18}$ forms together with the structural moiety —NH—CH—CO—$R_{19}$ the 2-carboxy-pyrrolidinyl-1-radical (prolinyl-(1)-radical) or the 4-hydroxy-prolinyl-(1)-radical, and $R_{20}$ represents OH or $C_1$–$C_6$-alkoxy, or the amide moiety is a dipeptide of said radical of —CO—NH—CH($R_{18}$)—CO—$R_{19}$ or a $C_1$–$C_6$-alkylester thereof, Z represents a sulphur atom or the group —S—C($R_5$)$_2$—, and the radicals $R_5$ are the same or different and represent hydrogen or $C_1$–$C_6$-alkyl and salts thereof with physiologically acceptable acids or cations.

2. A compound according to claim 1 where Z is a sulphur atom.

3. A compound according to claim 1 where Z is —S—C($R_5$)$_2$ and $R_5$ is hydrogen.

4. A compound according to claim 1 wherein $R_1$ and $R_2$ are both chlorethyl or $R_1$ is chloroethyl and $R_2$ is hydrogen, —CR$_5$R$_5$—CR$_5$R$_5$—is a 2 to 4 carbon atom alkyl group, Z is sulfur or S—CH$_2$—, all the $R_5$ groups attached to the heterocylic ring are hydrogen, $R_8$ is hydrogen, $C_2$–$C_6$-alkanoyl, glutamyl, the radical of glycine, proline, phenylalanine or tyrosine, $R_6$ is hydrogen and $R_7$ us a carboxyl group, a $C_1$–$C_6$alkoxycarbonyl group, a carboxyalkylamido group or $R_6$ and $R_7$ together form a ketone.

5. A pharmaceutical composition containing and effective amount of the compound according to claim 1 and a pharmaceutically acceptable carrier, diluent or auxiliary agent.

6. A method of inhibiting the proliferation of T-suppressor cells comprising administering to a mammal in need thereof a compound according to claim 1 in an amount effective to inhibit the proliferation of T-suppressor cells.

* * * * *